(12) United States Patent
Millerd

(10) Patent No.: US 8,062,265 B2
(45) Date of Patent: Nov. 22, 2011

(54) AUTOMATIC NEEDLE GUARD FOR MEDICATION PEN

(76) Inventor: Don Millerd, San Diego, CA (US)

( * ) Notice: Subject to any disclaimer, the term of this patent is extended or adjusted under 35 U.S.C. 154(b) by 545 days.

(21) Appl. No.: 11/267,830

(22) Filed: Nov. 4, 2005

(65) Prior Publication Data

US 2007/0106225 A1    May 10, 2007

(51) Int. Cl.
*A61M 5/32* (2006.01)
(52) U.S. Cl. .......................... 604/192; 604/198
(58) Field of Classification Search .................. 604/192, 604/197, 198, 263, 110, 162
See application file for complete search history.

(56) References Cited

U.S. PATENT DOCUMENTS

| | | | |
|---|---|---|---|
| 4,425,120 A | 1/1984 | Sampson et al. | |
| 4,664,654 A | 5/1987 | Strauss | |
| 4,681,567 A | 7/1987 | Masters et al. | |
| 4,911,693 A | 3/1990 | Paris | |
| 4,932,940 A * | 6/1990 | Walker et al. | 604/110 |
| 5,135,510 A * | 8/1992 | Maszkiewicz et al. | 604/195 |
| 5,222,945 A | 6/1993 | Basnight | |
| 5,232,457 A | 8/1993 | Grim | |
| 5,242,401 A * | 9/1993 | Colsky | 604/110 |
| 5,267,977 A | 12/1993 | Feeney, Jr. | |
| 5,292,314 A | 3/1994 | D'Alessio et al. | |
| 5,389,085 A | 2/1995 | D'Alessio et al. | |
| 5,549,558 A * | 8/1996 | Martin | 604/110 |
| 5,591,138 A | 1/1997 | Vaillancourt | |
| 5,695,475 A | 12/1997 | Best, Jr. et al. | |
| 6,162,197 A | 12/2000 | Mohammad | |
| 6,475,194 B2 | 11/2002 | Domici, Jr. et al. | |
| 6,648,858 B2 | 11/2003 | Asbaghi | |
| 6,884,237 B2 | 4/2005 | Asbaghi | |
| 2006/0189933 A1 | 8/2006 | Alheidt et al. | |

* cited by examiner

*Primary Examiner* — Theodore Stigell
*Assistant Examiner* — Bradley Osinski
(74) *Attorney, Agent, or Firm* — Ulmer & Berne, LLP

(57) ABSTRACT

A device for selectively protecting a needle includes an adapter holding the needle and a guard engaging the adapter for relative movement therebetween. Further, the device includes a means for guiding movement between the adapter and the guard. Structurally, the guiding means includes a "V" shaped slot in the guard and a radially-extending boss on the adapter. The boss is received in the slot to limit relative movement between the guard and the adapter. Specifically, in a first position of the device, the boss is in a first leg of the slot and the needle partially extends beyond the guard. In a second position, the boss is held at the apex of the slot and the needle fully extends beyond the guard. In a third position, the boss is in the second leg of the slot and the needle is retracted into the guard to protect the needle.

11 Claims, 3 Drawing Sheets

AUTOMATIC NEEDLE GUARD FOR MEDICATION PEN

FIELD OF THE INVENTION

The present invention pertains generally to needle protection devices. More particularly, the present invention pertains to needle protection devices that use a cylindrical guard to extend beyond the needle's tip to prevent contact with the tip. The present invention is particularly, but not exclusively useful as a needle protection device that uses cooperation between a "V" shaped slot and a radially-extending boss to limit relative movement between the guard and the needle.

BACKGROUND OF THE INVENTION

Needles are very common in medical practices, and are frequently used to deliver medications or to draw blood for diagnosis. As a result of their intensive use, it is estimated that some 600,000 to 800,000 accidental needle stick injuries occur every year. Further, there are roughly 8,000,000 healthcare workers in the United States who are at risk of being stuck with a contaminated needle. As the risks involved in providing medical treatment have risen and individual safety and sanitation are taken into consideration, disposable or single-use type of injection devices have become prevalent. While safer than reusable injection devices, these needles must still be handled carefully and the needle tips must be covered before and after use.

Although currently there exist various needle protection devices, most require the user to take an affirmative step to cover the needle tip after its use, thereby causing potential risk of contact with the needle. Other devices require specially designed needles, plungers, or medicament chambers.

In light of the above, it is an object of the present invention to provide a protective device that can be installed on a needle to ensure there is only a single use of the needle. It is another object of the present invention to provide a protective device having a guard that passively covers and protects the needle after an injection. It is another object of the present invention to provide a protective device that controls movement of the guard relative to the needle. Still another object of the present invention is to provide a protective device that requires an affirmative step to uncover the needle, but automatically covers the needle after an injection. Yet another object of the present invention is to provide a protective device for a needle that is relatively easy to manufacture, reliable and easy to use, and is comparatively cost effective.

SUMMARY OF THE INVENTION

In accordance with the present invention, a needle protection device includes an adapter for holding a needle. The device also includes a guard having a cylindrical wall that is dimensioned to engage the adapter for relative axial movement therebetween. Such movement is biased by a spring that urges the guard away from the adapter. Further, the guard includes an orifice for selectively passing the needle therethrough. In order to guide relative movement between the adapter and the guard, the guard is provided with a "V" shaped slot having a first leg and a second leg with an apex therebetween. Correspondingly, the adapter is provided with a radially-extending boss. The boss is received within the slot to limit relative movement between the guard and the adapter.

As a result of cooperation between the slot and the boss mentioned above, the device is only moveable from a first position to a second position, and from the second position to a third position. In the first position, the boss is in the first leg of the slot and the needle partially extends through the orifice of the guard. In the second position, the needle fully extends through the orifice of the guard and the boss is held at the apex of the slot in response to a force opposing the biasing means. In the third position, the boss is in the second leg of the slot and the needle is retracted into the guard to protect the needle.

For the purposes of the present invention, the boss is provided with an engagement face that is designed to interact with the slot to ensure that the boss moves to the end of the second leg from the apex during movement of the guard from the second position to the third position. Specifically, the face is inclined toward the second leg, so that contact between the face on the boss and the edge of the slot causes the boss to move toward the end of the second leg.

In order to protect the needle before use, the device may further include a removable shield. Structurally, the shield includes a hollow portion for receiving the needle. Further, the shield includes a radially extending rib that can be selectively positioned in the orifice of the guard to prevent axial movement of the guard from the first position to the second position.

For the present invention, the device may further include a locking mechanism that locks the device in the third position, to thereby prevent further relative movement between the guard and the adapter. Specifically, the adapter is provided with a shoulder that extends radially outward, and the guard is provided with an abutment that extends radially inward. When the device moves into the third position, the shoulder and the abutment engage one another to prevent further relative movement between the guard and the adapter.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1A:
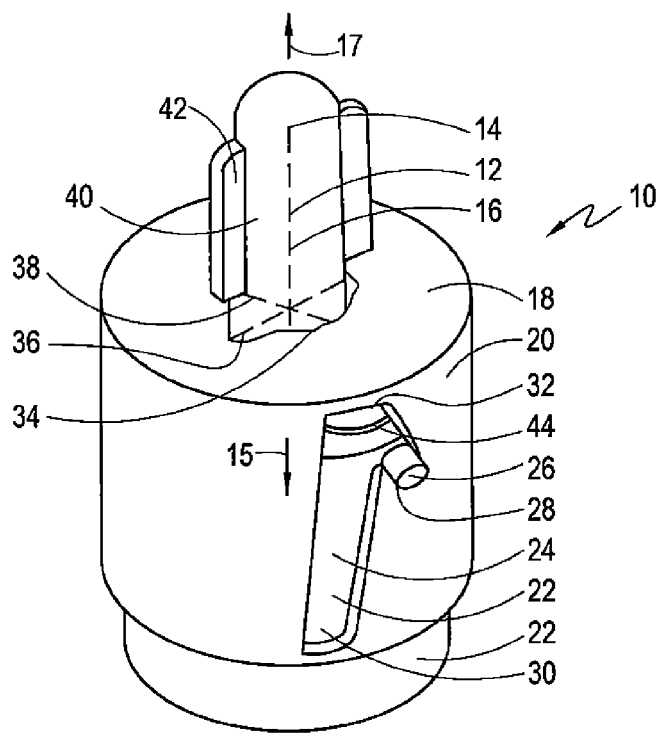
FIG. 1A is a perspective view of a needle protection device of the present invention.

Referring initially to FIG. 1A, a needle protection device in accordance with the present invention is shown and generally designated 10. As shown, the device 10 covers a needle 12 (shown in phantom) to prevent inadvertent contact with the needle tip 14. For discussion of the present invention, the needle 12 defines an axis 16, a proximal direction 15 and a distal direction 17. Structurally, the device 10 includes a guard 18 having a cylindrical wall 20 that slidingly engages an adapter 22. Further, the wall 20 includes a radially extending "V" shaped slot 24 that corresponds with and receives a boss 26 that extends radially outward from the adapter 22. The slot 24 includes a first leg 28 which meets a longer second leg 30 at an apex 32. As shown, the boss 26 is positioned in the first leg 28 of the slot 24. For the purposes of the present invention, the slot 24 and boss 26 cooperate to guide axial movement of the guard 18 relative to the adapter 22.

Still referring to FIG. 1A, the guard 18 is shown as including an axially extending orifice 34 that is formed with a long axis 36 and a short axis 38. In addition to the guard 18 and the adapter 22, the device 10 includes a removable shield 40. In FIG. 1A, the shield 40 is shown passing through the orifice 34 and including radially extending grips 42 to facilitate rotation of the shield 40 about the axis 16 as discussed below. As shown, the device 10 further includes a spring 44 that biases the guard 18 away from the adapter 22.

Figure 1B:
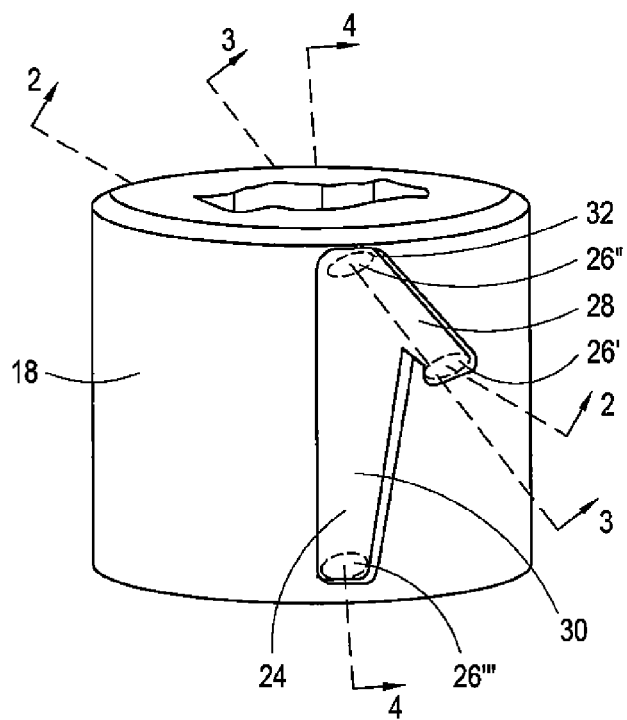
FIG. 1B is a perspective view of the guard shown in FIG. 1A, illustrating the movement of the boss in the "V" shaped slot.

Referring to FIG. 1B, the boss 26' is positioned in the first leg 28 of the slot 24 (i.e., the first position of the device 10), the boss 26" is positioned at the apex 32 of the slot 24 (i.e., the second position of the device 10), and the boss 26''' is positioned in the second leg 30 of the slot 24 (i.e., the third position of the device 10). As can be understood from cross-referencing FIG. 1A with FIG. 1B, movement of the boss 26 between these positions results in rotational movement of the guard 18 about the axis 16 relative to the adapter 22, particularly during movement from boss 26' to boss 26".

Figure 2A:
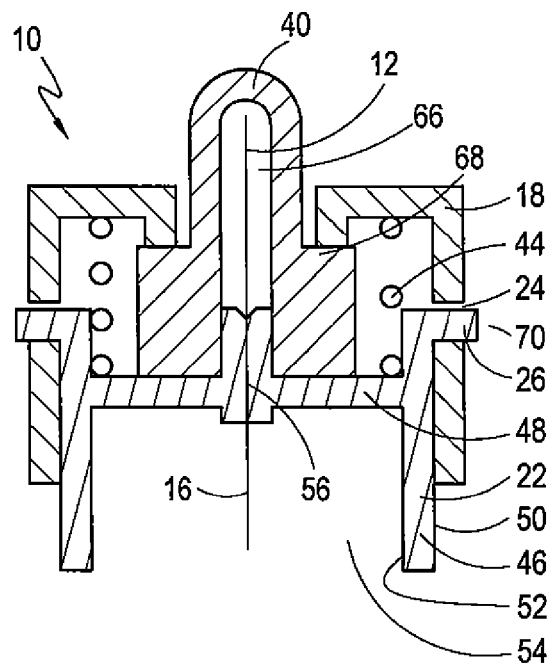
FIG. 2A is a cross section view of the needle protection device of FIG. 1A, as seen along line 2-2 in FIG. 1B.
Figure 2B:
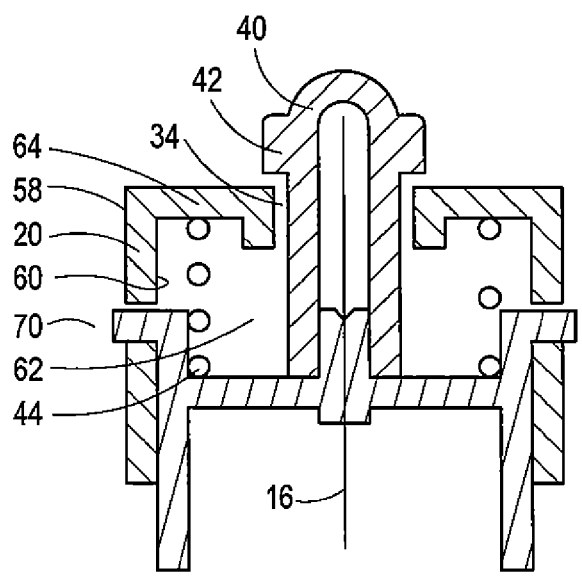
FIG. 2B is a cross section view of the needle protection device of FIG. 2A with the removable shield rotated for removal in accordance with the present invention.

Referring now to FIGS. 2A and 2B, internal components and features of the device 10 can be seen. As shown, the adapter 22 includes an axially-extending and substantially cylindrical base member 46 centered about the axis 16. Further, the adapter 22 includes a radially-extending cap member 48. As shown, the adapter 22 has an external surface 50 and an internal surface 52, with the internal surface 52 defining an internal cavity 54. As further shown, the needle 12 passes through an aperture 56 formed in the cap member 48.

Turning to the guard 18, it can be seen from FIGS. 2A and 2B, that the cylindrical wall 20 includes an outer side 58 and an inner side 60. As shown, the inner side 60 defines a chamber 62 in which the adapter 22 is partially received. The chamber 62 is further bounded by an end member 64 mounted to the cylindrical wall 20 and forming the orifice 34. For the purposes of the invention, the spring 44 is positioned in the chamber 62 between the cap member 48 of the adapter 22 and the end member 64 of the guard 18 to bias the guard 18 axially away from the adapter 22.

As further shown in FIGS. 2A and 2B, the device 10 includes a removable shield 40 having a hollow portion 66 for receiving the needle 12. As shown in FIG. 2A, the shield 40 includes radially extending ribs 68 that are engaged with the guard 18 and the adapter 22. In the orientation of FIG. 2A, the ribs 68 prevent axial movement of the guard 18 toward the adapter 22. Cross-referencing FIG. 2A with FIG. 2B, it can be seen that the ribs 68 may be removed from contact with the guard 18. Specifically, FIG. 2B depicts the shield 40 of FIG. 2A after the shield 40 has been rotated ninety degrees about the axis 16. As a result, the ribs 68 are aligned with the long axis 36 of the orifice 34 (see FIG. 1A) and the shield 40 may be removed from the device 10.

Typically, the device 10 is stored and transported in the orientation shown in FIG. 2A. Before the needle 12 is used for an injection, the shield 40 is rotated as in FIG. 2B and is removed. Regardless of the position of the shield 40, each of FIGS. 1A, 2A and 2B depict the device in a first position 70 in which the boss 26 is received within the first leg 28 of the slot 24. After the shield 40 is removed, the guard 18 may be moved in the proximal direction 15 toward the adapter 22 if a sufficient force is applied thereto. Specifically, if a force greater than the biasing force of the spring 44 is applied.

Figure 3:
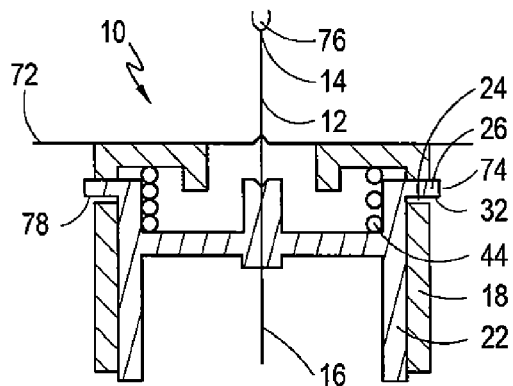
FIG. 3 is a cross section view of the needle protection device of FIG. 2B, as seen along line 3-3 in FIG. 1B, with the shield removed and the needle inserted into a subject in accordance with the present invention.

In FIG. 3, the result of an application of such a force is shown. As shown, the needle 12 has been injected into a subject 72. As a result, the force of the subject 72 on the guard 18 has caused the guard 18 to move toward the adapter 22. Specifically, the device 10 has moved to the second position 74 in which the boss 26 is positioned at the apex 32 of the slot 24. When the boss 26 reaches the apex 32, further movement of the guard 18 toward the adapter 22 is prevented by the interaction between the slot 24 and the boss 26.

After the needle 12 has injected a fluid 76 into the subject 72, the needle 12 is withdrawn from the subject 72. During withdrawal, the spring 44 pushes the guard 18 away from the adapter 22. At the same time, the boss 26 moves from the apex 32 to the second leg 30 (as shown in FIG. 4A).

To ensure that the boss 26 moves to the end of the second leg 30 rather than back to the first leg 28, the boss 26 is provided with an engagement face 78. The face 78 is inclined toward the second leg 30 so that when the boss 26 moves out of the apex 32 it slides to the end of the second leg 30.

Figure 4A:
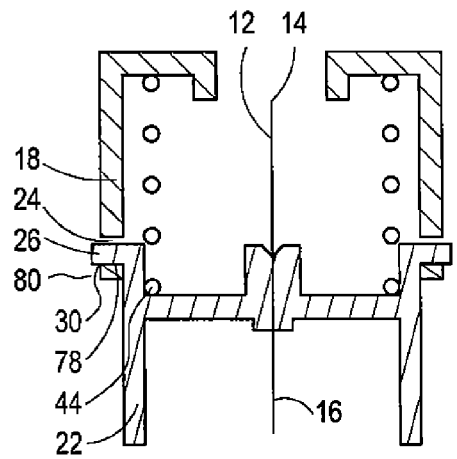
FIG. 4A is a cross section view of the needle protection device of FIG. 3, as seen along line 4-4 in FIG. 1B, with the needle withdrawn from the subject and the guard advanced to cover the needle tip in accordance with the present invention.
Figure 4B:
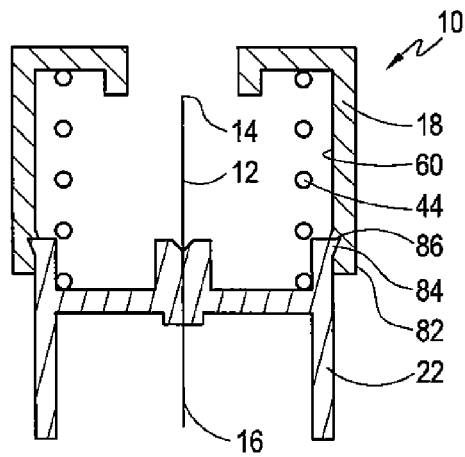
FIG. 4B is a cross section view of the needle protection device of FIG. 4A, as seen from a view taken ninety degrees from the view in FIG. 4A.

Referring now to FIG. 4A, the device 10 is shown in its third position 80 with the boss 26 in the second leg 30. As shown, the guard 18 is extended and fully covers the needle tip 14. In order to prevent any further use of the needle 12, the device 10 is provided with the locking mechanism 82 seen in FIG. 4B. FIG. 4B is a cross section view of the device 10 taken from a view ninety degrees from the view in FIG. 4A. Approximately ninety degrees from the bosses 26 shown in FIG. 4A are two shoulders 84 shown in FIG. 4B that extend radially outward from the adapter 22. As further seen in FIG. 4B, the device 10 includes two corresponding abutments 86 that extend radially inward from the guard 18. As shown, the shoulders 84 and abutments 86 are tapered. This construction allows the shoulders 84 to slide in the proximal direction 15 along the inner side 60 of the guard 18 until they pass the abutments 86. Once the shoulders 84 pass the abutments 86, the guard 18 can no longer be moved toward the adapter 22. As a result, the device 10 is locked with the needle 12 protected by the guard 18.

Figure 5:
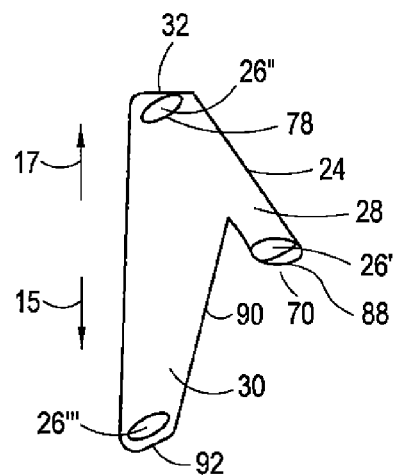
FIG. 5 is a side view of the slot and boss arrangement showing the configuration of the slot and the boss in the first, second and third positions.

Referring now to FIG. 5, the interaction between the slot 24 and the boss 26 can be clearly shown. In FIG. 5, the boss 26 is shown in the various stations (indicated by 26', 26", and 26''') it passes through during operation of the device 10. Specifically, the boss 26' is shown in the first leg 28 adjacent the first stop 88 when the device 10 is in the first position 70. The first stop 88 may serve to prevent axial movement of the guard 18 away from the adapter 22. As noted above, the shield 40 prevents axial movement of the guard 18 toward the adapter 22 when the ribs 68 are positioned between the guard 18 and adapter 22. When the ribs 68 are disengaged from the guard 18 and the shield 40 has been removed, the spring 44 retains the boss 26' in the first leg 28.

When a force is applied to the guard 18 in the proximal direction 15 to move the guard 18 toward the adapter 22, i.e., during an injection, the boss 26' moves from the first stop 88 to its position as boss 26" at the apex 32. Movement of the guard 18 toward the adapter 22 may be stopped by contact between the boss 26" and the apex 32, or by contact between other components in the device 10.

When the force in the proximal direction 15 is removed, i.e., during withdrawal of the needle 12 from the subject 72, the spring 44 forces the guard 18 away from the adapter 22 in the distal direction 17. As a result, the boss 26" moves axially away from the apex 32 to its position at boss 26''' in the second leg 30 of the slot 24. As indicated by FIG. 5, during movement from boss 26" to boss 26''', the engagement face 78 may contact the edge 90 of the slot 24. Due to the inclination of the engagement face 78 toward the second leg 30 and the slope of the edge 90 of the slot 24, contact between the boss 26 and the edge 90 of the slot 24 causes the boss 26 to move to the second stop 92 of the second leg 30. Alternatively, the boss 26" may move substantially in the proximal direction 15 directly to the second stop 92 of the second leg 30. In either case, the spring 44 forces the guard 18 away from the adapter 22 until the boss 26''' contacts the second stop 92 or until further axial movement of the guard 18 away from the adapter 22 is otherwise prevented. As shown in FIG. 4B, the locking mechanism 82 then prevents any further relative movement between the guard 18 and the adapter 22.

While the particular Automatic Needle Guard for Medication Pen as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims. Further, it is contemplated that the boss and slot cooperating structures may be reversed such that the boss be formed on the guard and the slot be formed in the adapter. Such an embodiment is considered to be an equivalent combination of structure to the specific embodiment disclosed and claimed herein.

What is claimed is:

1. A device for selectively protecting a needle which comprises:
    an adapter for holding the needle, wherein the needle defines an axis and the adapter is formed with a boss extending in a radial direction therefrom and wherein the boss is formed with an inclined engagement face;
    a guard formed with an orifice for passing the needle therethrough and having a cylindrical wall dimensioned to engage said adapter for relative axial movement therebetween, wherein the wall is formed with a "V" shaped slot having a first leg and a second leg with an apex therebetween, with the boss of said adapter inserted into the slot of said guard;
    a spring positioned between the guard and the adapter with the guard surrounding the spring for biasing the guard away from the adapter during an axial movement of the guard from a first position wherein the boss is in the first leg of the slot and the needle partially extends through the orifice of the guard, to a second position wherein the needle fully extends through the orifice of the guard and the boss is held at the apex of the slot in response to a force opposing said biasing means, and thereafter to a third position as the inclined engagement face of the boss interacts with the slot to move the boss into the second leg of the slot for retraction of the needle into the guard to protect the needle and;
    a removable shield for preventing contact with the needle before an injection, said shield forming a hollow portion for receiving the needle, said shield being selectively positioned in the orifice of the guard to prevent any axial movement of said guard from the first position to the second position, wherein said removable shield comprises at least a rib positioned between said guard and said adapter to prevent axial movement of said guard from the first position to the second position.

2. A device as recited in claim 1 wherein the first leg of the slot is shorter than the second leg of the slot.

3. A device as recited in claim 1 further comprising a means for locking the guard in the third position to prevent further relative movement between the guard and the adapter.

4. A device as recited in claim 3 wherein said locking means includes a shoulder radially extending from the adapter and an abutment radially extending from the guard, and wherein said shoulder engages said abutment when the guard is in the third position.

5. A device as recited in claim 1 wherein the guard includes two circumferentially-spaced "V" shaped slots and the adapter includes two corresponding circumferentially-spaced bosses, with each slot receiving a respective boss therein.

6. A device as recited in claim 5 wherein the cylindrical wall of the guard has an inner side defining a chamber, the adapter has an external surface, and the adapter is received within the chamber with the inner side of the guard engaging the external surface of the adapter, and wherein the boss extends from the external surface into the slot of the guard.

7. A device as recited in claim 1 wherein the rib of the shield comprises a radially extending rib, said rib engaging the guard and the adapter to prevent axial movement of the guard from the first position to the second position when the shield is selectively positioned in the orifice of the guard.

8. A device for selectively protecting a needle which comprises:
    a means for holding the needle, wherein the needle defines an axis, with said holding means including a radially-extending boss and wherein the boss is formed with an inclined engagement face;
    a means for guarding the needle, said guarding means forming an orifice for passing the needle therethrough and engaging said holding means for relative axial movement therebetween, with said guarding means including a "V" shaped slot with the radially-extending boss received therein, with said slot having a first leg and a second leg with an apex therebetween; and
    a means for biasing the guarding means away from the holding means, wherein the guarding means surrounds the biasing means during an axial movement of the guarding means from a first position wherein the boss is in the first leg of the slot and the needle partially extends through the orifice of the guarding means, to a second position wherein the needle fully extends through the orifice of the guarding means and the boss is held at the apex of the slot in response to a force opposing said biasing means, and thereafter to a third position as the inclined engagement face of the boss interacts with the slot to move the boss into the second leg of the slot for retraction of the needle into the guarding means to protect the needle and;
    a removable shield for preventing contact with the needle before an injection, said shield forming a hollow portion for receiving the needle, said shield being selectively positioned in the orifice of the guard to prevent any axial movement of said guard from the first position to the second position, wherein said removable shield comprises at least a portion positioned between said guard and said adapter to prevent axial movement of said guard from the first position to the second position.

9. A device as recited in claim 8 further comprising a means for locking the guarding means in the third position to prevent further relative movement between the guarding means and the holding means.

10. A device as recited in claim 9 wherein said locking means includes a shoulder radially extending from the holding means and an abutment radially extending from the guarding means, and wherein said shoulder engages said abutment when the guarding means is in the third position.

11. A device as recited in claim 8 wherein said removable shield includes a radially extending rib, said rib engaging the guarding means and the holding means to prevent axial movement of the guarding means from the first position to the second position when the removable shield is selectively positioned in the orifice of the guarding means.

* * * * *